US010111586B2

(12) United States Patent
Li et al.

(10) Patent No.: US 10,111,586 B2
(45) Date of Patent: Oct. 30, 2018

(54) FORWARD AND SIDE IMAGING OPTICAL COHERENCE TOMOGRAPHY PROBE

(71) Applicant: SYNAPTIVE MEDICAL (BARBADOS) Inc., Bridgetown (BB)

(72) Inventors: Fangxin Li, Toronto (CA); Michael Frank Gunter Wood, Toronto (CA)

(73) Assignee: SYNAPTIVE MEDICAL (Barbados) Inc., Bridgetown (BB)

( * ) Notice: Subject to any disclaimer, the term of this patent is extended or adjusted under 35 U.S.C. 154(b) by 0 days.

(21) Appl. No.: 15/105,752

(22) PCT Filed: Sep. 2, 2015

(86) PCT No.: PCT/IB2015/056670
§ 371 (c)(1),
(2) Date: Jun. 17, 2016

(87) PCT Pub. No.: WO2017/037507
PCT Pub. Date: Mar. 9, 2017

(65) Prior Publication Data
US 2017/0202451 A1    Jul. 20, 2017

(51) Int. Cl.
*A61B 5/05* (2006.01)
*A61B 3/10* (2006.01)
(Continued)

(52) U.S. Cl.
CPC .......... *A61B 3/102* (2013.01); *A61B 1/00096* (2013.01); *A61B 1/00172* (2013.01);
(Continued)

(58) Field of Classification Search
CPC ............ A61B 1/00096; A61B 1/00172; A61B 5/0062; A61B 5/6852
See application file for complete search history.

(56) References Cited

U.S. PATENT DOCUMENTS

2006/0241503 A1* 10/2006 Schmitt ............... A61B 5/0066
600/478
2010/0125170 A1* 5/2010 Sugimoto ............ A61B 1/0008
600/178
(Continued)

FOREIGN PATENT DOCUMENTS

JP    2001264246 A    9/2001
JP    2010533301 A    10/2010

OTHER PUBLICATIONS

Oprea, Karen. International Search Report, PCT International Application No. PCT/IB2015/056670, dated May 27, 2016.

*Primary Examiner* — Amelie R Gillman
(74) *Attorney, Agent, or Firm* — Perry + Currier Inc.

(57) ABSTRACT

A forward-imaging optical coherence tomography probe is provided, comprising: a substantially cylindrical housing comprising: a longitudinal axis; an interior side; a distal end that is optically transparent; and a mirror located at the interior side, adjacent the distal end; an optical fiber located inside the cylindrical housing along the longitudinal axis; a wedge lens located inside the cylindrical housing, adjacent the distal end, the wedge lens configured to receive light from the fiber, and direct the light towards the mirror; and, at least one motor configured to both: rotate the fiber and the wedge lens about the longitudinal axis and inside the cylindrical housing; and, linearly displace the fiber and the wedge lens along the longitudinal axis and inside the cylindrical housing; the mirror configured to: receive light from the wedge lens and reflect the light out of the distal end as the wedge lens moves linearly and rotationally.

5 Claims, 16 Drawing Sheets

(51) Int. Cl.
*A61B 1/00* (2006.01)
*A61B 5/00* (2006.01)
(52) U.S. Cl.
CPC .......... *A61B 5/0062* (2013.01); *A61B 5/0066* (2013.01); *A61B 5/6852* (2013.01)

(56) References Cited

U.S. PATENT DOCUMENTS

| | | | |
|---|---|---|---|
| 2010/0286531 A1* | 11/2010 | Ryan | A61B 5/0066 600/478 |
| 2012/0041290 A1* | 2/2012 | Perelman | A61B 5/0062 600/326 |
| 2012/0080612 A1* | 4/2012 | Grego | A61B 1/0008 250/458.1 |
| 2014/0031677 A1* | 1/2014 | Iftimia | A61B 5/0066 600/425 |
| 2014/0100449 A1* | 4/2014 | Begin | A61B 8/0841 600/424 |
| 2015/0055093 A1* | 2/2015 | Ehlers | A61B 3/102 351/206 |

* cited by examiner

FORWARD AND SIDE IMAGING OPTICAL COHERENCE TOMOGRAPHY PROBE

FIELD

The specification relates generally to optical coherence tomography probes and methods for minimally invasive therapy and image guided medical procedures, and specifically to a forward-imaging optical coherence tomography (OCT) probe for use in a medical procedure.

BACKGROUND

The low penetration depth of optical waves (generally about 200 nm to about 2 μm) in tissue (i.e. generally about 2 mm to about 3 mm) limits the clinical application of optical imaging instrumentations, such as optical coherence tomography (OCT), and the like. Therefore, hand-held or endoscopic probes are highly desired for clinical and therapeutic applications, however such probes tend to suffer from various problems.

OCT probes, and the like, can be divided into two categories based on their scan modes: side imaging and forward imaging. Side-imaging probes are the most widely used since they tend to have a much simpler actuation mechanism than forward-imaging probes, and the actuation mechanism tends to be far away from the probe tips. Further, side-imaging probes tend to be very flexible and have small size. However, such side-imaging scanning probes only provide side imaging around the probe which limits its clinical applications, such as image-based surgical needle guidance. Thus, forward-imaging probes, whose size tends to be in a range of needle size, can be more suitable for surgical guidance for brain, retinal and ovarian surgery.

However, forward-imaging probes are generally more complicated in design and require the actuator near the probe tips. Currently the size of the forward-imaging OCT probe is mainly limited by the size of the actuation mechanism. For example, forward-imaging probes using MEMS (micro-electromechanical system) mirrors generally have a diameter in a range of about 3 mm to about 6 mm due to the electronic control cable used with forward-imaging probe. Further, forward-imaging probe are generally housed in a thin-wall hypodermic tube using a PZT actuator with an overall diameter of about 2.4 mm.

SUMMARY

The present disclosure is generally directed to image guided medical procedures which may or may not use an access port. A port-based surgery approach allows a surgeon, or robotic surgical system, to perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

Furthermore, a forward-imaging optical coherence tomography (OCT) probe, for use in a medical procedure, is provided which includes a optical fiber coupled to a wedge lens inside a substantially cylindrical housing, the housing having an optically transparent distal end, with a mirror on an exterior side of the housing adjacent the distal end. The probe includes a motor which can move the fiber and the wedge lens linearly within the housing and also rotate the fiber and the wedge lens. Light from the fiber is emitted by the wedge lens at an angle to a longitudinal axis of the housing towards the mirror, and reflects from the mirror out of the distal end. As the wedge lens rotates, and moves linearly within the housing, an area of a sample (adjacent the distal end) that is illuminated by the light, changes. Specifically, when the mirror comprises a ring mirror, a spiral of illumination occurs, and/or successive rings (and/or circles) of illumination occur, at the sample as the wedge lens rotates and moves linearly, hence both forward and side illumination occurs. Even better coverage of the sample can be provided by when the mirror comprises a graded-radius cylindrical reflection mirror, with a widest radius adjacent the distal end.

Further provided herein is a kit for adapting an existing side-imaging OCT probe to a forward-imaging OCT probe, the kit comprising the housing and the motor as described above. Such a kit can be provided and installed at an existing side-imaging OCT probe comprising a fiber and a wedge lens. Instructions for adapting an OCT interferometer for use with an adapted probe can also be provided, the instructions including instructions for processing captured OCT images using an adapted probe.

An aspect of the specification provides a forward-imaging optical coherence tomography (OCT) probe for use in a medical procedure, comprising: a substantially cylindrical housing comprising: a longitudinal axis; an interior side; a distal end that is optically transparent; and a mirror located at the interior side, adjacent the distal end; an optical fiber located inside the cylindrical housing along the longitudinal axis; a wedge lens located inside the cylindrical housing, adjacent the distal end, the wedge lens configured to receive light from the optical fiber, and direct the light towards the mirror; and, at least one motor configured to both: rotate the optical fiber and the wedge lens about the longitudinal axis and inside the cylindrical housing; and, linearly displace the optical fiber and the wedge lens along the longitudinal axis and inside the cylindrical housing; the mirror configured to: receive light from the wedge lens and reflect the light out of the distal end as the wedge lens moves linearly and rotationally.

The forward-imaging OCT probe can further comprise a power supply configured to power at least the at least one motor.

The forward-imaging OCT probe can further comprise one or more computing devices configured to one or more of: control the at least one motor; and process OCT images received back from the optical fiber as the optical fiber is moving.

The forward-imaging OCT probe can further comprise at least one OCT interferometer in communication with the optical fiber.

The mirror can comprise a ring mirror.

The mirror can comprise a graded-radius cylindrical reflection mirror, with a widest radius adjacent the distal end.

The mirror can be at 45° to the longitudinal axis, and the wedge lens can be configured to direct the light towards the mirror at 90° to the longitudinal axis.

The mirror can comprise a parabolic mirror, with a widest radius adjacent the distal end, and the wedge lens can be configured to direct the light towards the mirror at 90° to the longitudinal axis.

The forward-imaging OCT probe can further comprise at least one GRIN (graded index) lens between an exit face of the optical fiber and the wedge lens, the at least one GRIN lens configured to focus the light from the exit face into the wedge lens.

The forward-imaging OCT probe can further comprise an optical coupler configured to couple a second optical fiber to an entrance face of the optical fiber, the second optical fiber configured to convey the light from an OCT interferometer to the optical fiber. The forward-imaging OCT probe can further comprise at least one GRIN (graded index) lens between the optical coupler and the entrance face of the optical fiber, the at least one GRIN lens configured to focus the light from the optical coupler into the optical fiber. The at least one motor can comprise a linear motor and a rotational motor.

Another aspect of the specification provides a kit for adapting an OCT probe for depth and surface profiling, the OCT probe comprising an optical fiber in optical communication with a wedge lens, the kit comprising: a cylindrical housing comprising: a longitudinal axis; an interior side; a distal end that is optically transparent; and a mirror located at the interior side, adjacent the distal end; the cylindrical housing configured to accept therein: the optical fiber located along the longitudinal axis; and, the wedge lens located inside adjacent the distal end, the mirror configured to: receive light from the wedge lens and reflect the light out of the distal end; and, at least one motor connectable to the optical fiber, the at least one motor configured to both: rotate the optical fiber and the wedge lens about the longitudinal axis and inside the cylindrical housing; and, linearly displace the optical fiber and the wedge lens along the longitudinal axis and inside the cylindrical housing; the mirror configured to: receive light from the wedge lens and reflect the light out of the distal end as the wedge lens moves linearly and rotationally.

The mirror can comprise one or more of a ring mirror, and a mirror at 45° to the longitudinal axis.

The mirror can comprise a parabolic mirror, with a widest radius adjacent the distal end.

BRIEF DESCRIPTIONS OF THE DRAWINGS

For a better understanding of the various implementations described herein and to show more clearly how they may be carried into effect, reference will now be made, by way of example only, to the accompanying drawings in which.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

The systems and methods described herein may be useful in the field of neurosurgery, including oncological care, neurodegenerative disease, stroke, brain trauma and orthopedic surgery; however persons of skill will appreciate the ability to extend these concepts to other conditions or fields of medicine. It should be noted that the surgical process is applicable to surgical procedures for brain, spine, knee and any other suitable region of the body.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

Figure 1:
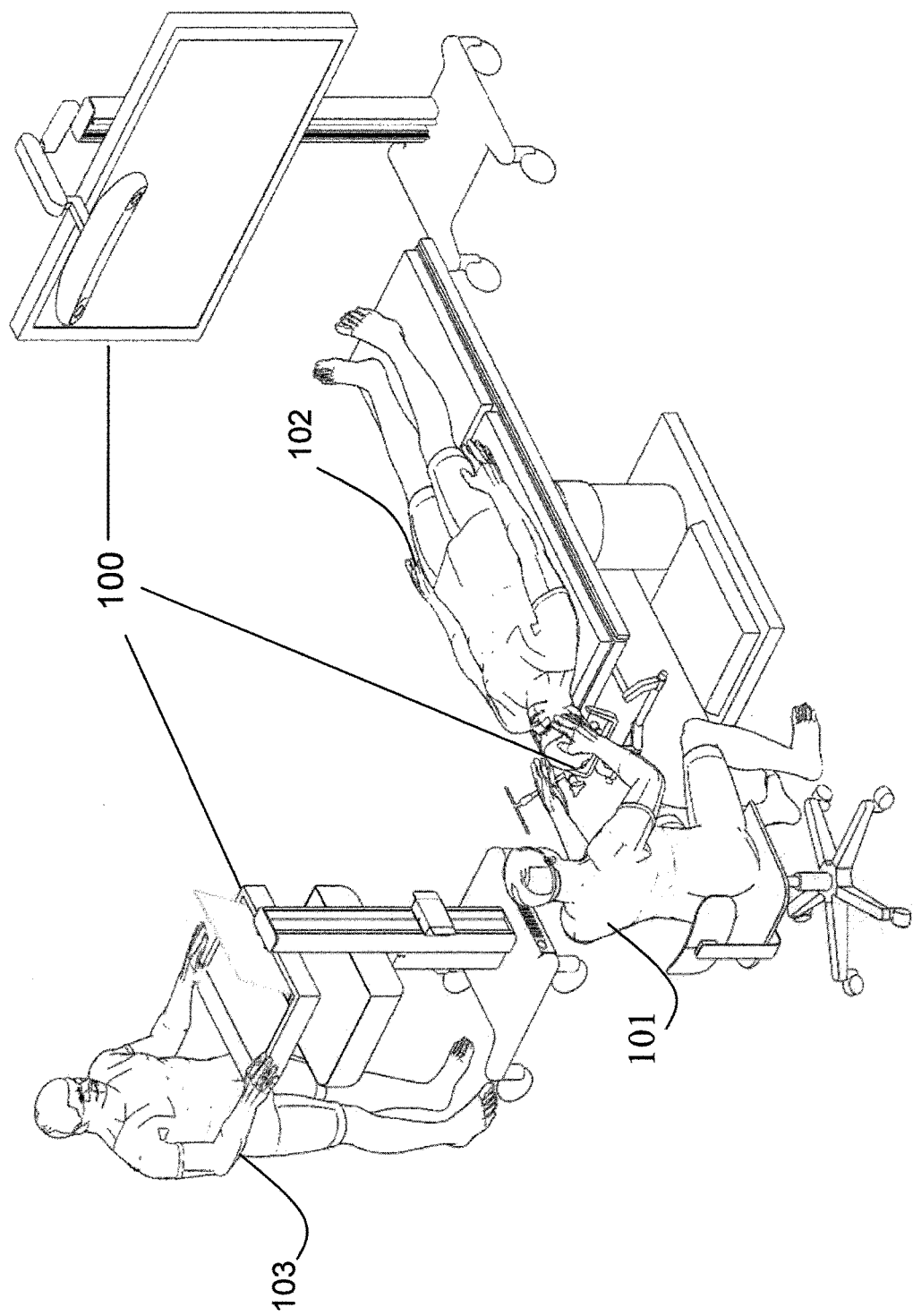
FIG. 1 shows an example operating room setup for a minimally invasive access port-based medical procedure, according to non-limiting implementations.

Referring to FIG. 1, a non-limiting example navigation system 100 is shown to support minimally invasive access port-based surgery or surgical corridor-based surgery. In FIG. 1, a neurosurgeon 101 conducts a minimally invasive port-based surgery on a patient 102 in an operating room (OR) environment. The navigation system 100 includes an equipment tower, tracking system, displays and tracked instruments to assist the surgeon 101 during the procedure. An operator 103 may also be present to operate, control and provide assistance for the navigation system 100.

Figure 2:
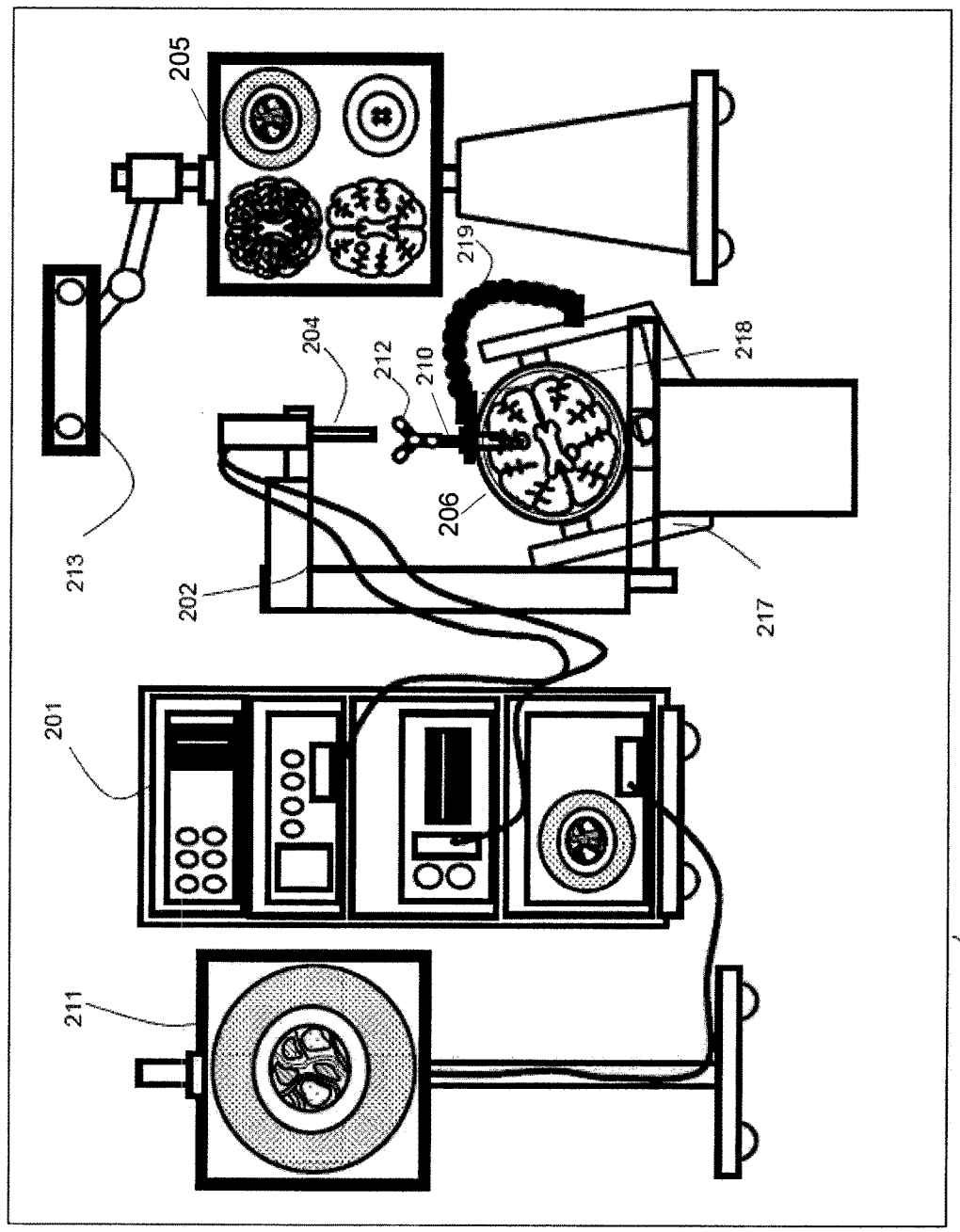
FIG. 2 is a block diagram illustrating components of a medical navigation system that may be used to implement a surgical plan for a minimally invasive surgical procedure, according to non-limiting implementations.

Referring to FIG. 2, a block diagram is shown illustrating components of an example medical navigation system 200, according to non-limiting implementations. The medical navigation system 200 illustrates a context in which a surgical plan including equipment (e.g., tool and material) tracking, such as that described herein, may be implemented. The medical navigation system 200 includes, but is not limited to, one or more monitors 205, 211 for displaying a video image, an equipment tower 201, and a mechanical arm 202, which supports an optical scope 204. The equipment tower 201 may be mounted on a frame (e.g., a rack or cart) and may contain a computer or controller (examples provided with reference to FIGS. 3 and 6 below), planning software, navigation software, a power supply and software to manage the mechanical arm 202, and tracked instruments. In one example non-limiting implementation, the equipment tower 201 may comprise a single tower configuration with dual display monitors 211, 205, however other configurations may also exist (e.g., dual tower, single display, etc.). Furthermore, the equipment tower 201 may also be configured with a universal power supply (UPS) to provide for emergency power, in addition to a regular AC adapter power supply.

A patient's anatomy may be held in place by a holder. For example, in a neurosurgical procedure the patient's head may be held in place by a head holder 217, and an access port 206 and an introducer 210 may be inserted into the patient's head. The introducer 210 may be tracked using a tracking camera 213, which provides position information for the navigation system 200. The tracking camera 213 may also be used to track tools and/or materials used in the surgery, as described in more detail below. In one example non-limiting implementation, the tracking camera 213 may comprise a 3D (three-dimensional) optical tracking stereo camera, similar to one made by Northern Digital Imaging (NDI), configured to locate reflective sphere tracking markers 212 in 3D space. In another example, the tracking camera 213 may comprise a magnetic camera, such as a field transmitter, where receiver coils are used to locate objects in 3D space, as is also known in the art. Location data of the mechanical arm 202 and access port 206 may be determined by the tracking camera 213 by detection of tracking markers 212 placed on these tools, for example the introducer 210 and associated pointing tools. Tracking markers may also be placed on surgical tools or materials to be tracked. The secondary display 205 may provide output of the tracking camera 213. In one example non-limiting implementation, the output may be shown in axial, sagittal and coronal views as part of a multi-view display.

As noted above with reference to FIG. 2, the introducer 210 may include tracking markers 212 for tracking. The tracking markers 212 may comprise reflective spheres in the case of an optical tracking system and/or pick-up coils in the case of an electromagnetic tracking system. The tracking markers 212 may be detected by the tracking camera 213 and their respective positions are inferred by the tracking software.

As shown in FIG. 2, a guide clamp 218 (or more generally a guide) for holding the access port 206 may be provided. The guide clamp 218 may optionally engage and disengage with the access port 206 without needing to remove the access port 206 from the patient. In some examples, the access port 206 may be moveable relative to the guide clamp 218, while in the guide clamp 218. For example, the access port 206 may be able to slide up and down (e.g., along the longitudinal axis of the access port 206) relative to the guide clamp 218 while the guide clamp 218 is in a closed position. A locking mechanism may be attached to or integrated with the guide clamp 218, and may optionally be actuatable with one hand, as described further below. Furthermore, an articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g., on another patient support, such as on the surgical bed), to ensure that when locked in place, the guide clamp 218 does not move relative to the patient's head.

Figure 3:
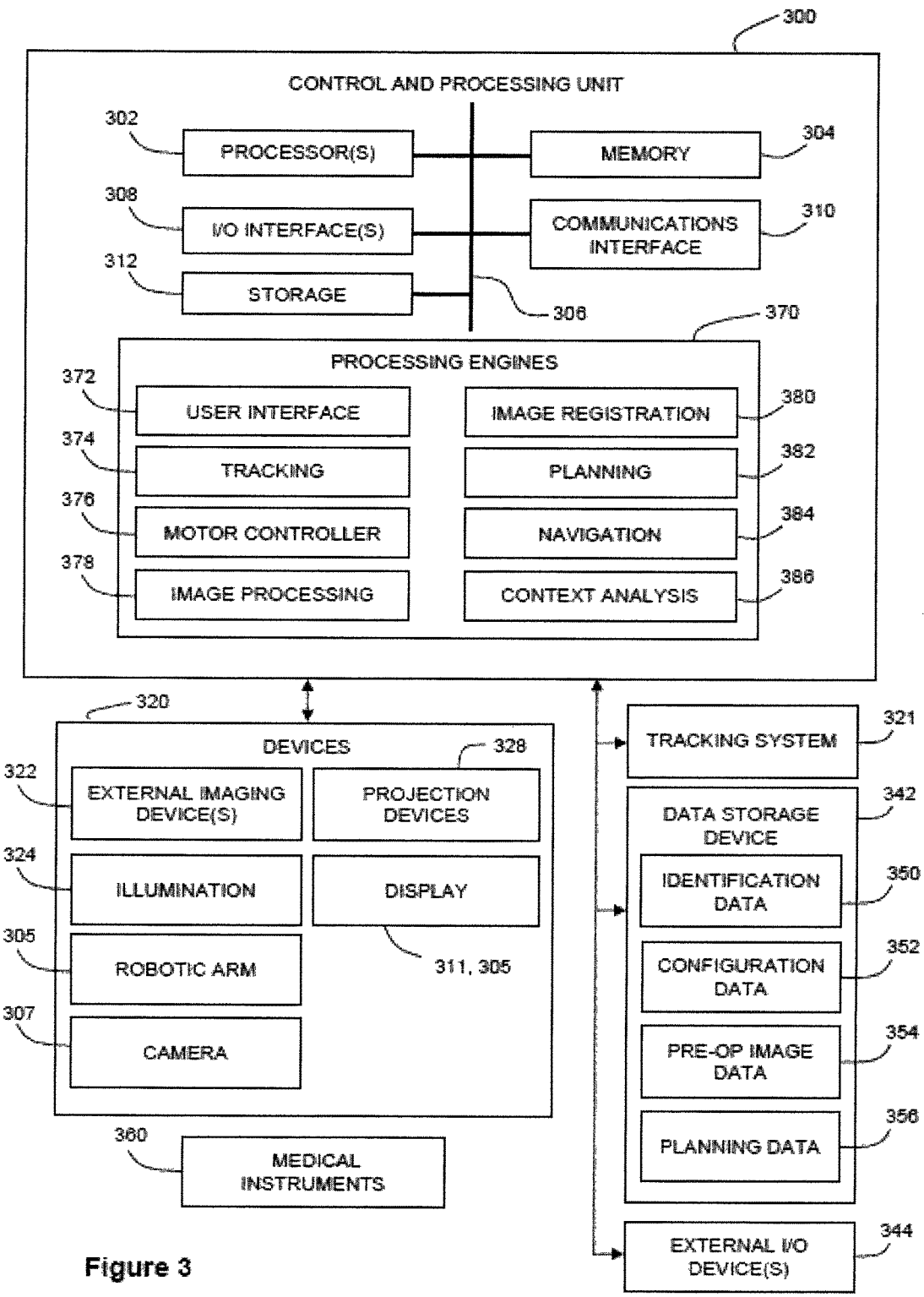
FIG. 3 depicts a block diagram illustrating components of a planning system used to plan a medical procedure that may then be implemented using the navigation system of FIG. 2, according to non-limiting implementations.

Referring to FIG. 3, a block diagram is shown illustrating a control and processing unit 300 that may be used in the navigation system 200 of FIG. 2 (e.g., as part of the equipment tower). In one example non-limiting implementation, control and processing unit 300 may include one or more processors 302, a memory 304, a system bus 306, one or more input/output interfaces 308, a communications interface 310, and storage device 312. In particular, one or more processors 302 may comprise one or more hardware processors and/or one or more microprocessors. Control and processing unit 300 may be interfaced with other external devices, such as tracking system 321, data storage device 342, and external user input and output devices 344, which may include, but is not limited to, one or more of a display, keyboard, mouse, foot pedal, and microphone and speaker. Data storage device 342 may comprise any suitable data storage device, including, but not limited to a local and/or remote computing device (e.g. a computer, hard drive, digital media device, and/or server) having a database stored thereon. In the example shown in FIG. 3, data storage device 342 includes, but is not limited to, identification data 350 for identifying one or more medical instruments 360 and configuration data 352 that associates customized configuration parameters with one or more medical instruments 360. Data storage device 342 may also include, but is not limited to, preoperative image data 354 and/or medical procedure planning data 356. Although data storage device 342 is shown as a single device in FIG. 3, in other implementations, data storage device 342 may be provided as multiple storage devices.

Medical instruments 360 may be identifiable using control and processing unit 300. Medical instruments 360 may be connected to and controlled by control and processing unit 300, and/or medical instruments 360 may be operated and/or otherwise employed independent of control and processing unit 300. Tracking system 321 may be employed to track one or more of medical instruments 360 and spatially register the one or more tracked medical instruments 360 to an intraoperative reference frame. In another example, a sheath may be placed over a medical instrument 360 and the sheath may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include, but are not limited, one or more external imaging devices 322, one or more illumination devices 324, a robotic arm, one or more projection devices 328, and one or more displays 305, 311.

Aspects of the specification may be implemented via processor(s) 302 and/or memory 304. For example, the functionalities described herein may be partially implemented via hardware logic in processor 302 and partially using the instructions stored in memory 304, as one or more processing modules 370 and/or processing engines. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example non-limiting implementation the processing modules 370 may be stored in the memory 304 and the processing modules may be collectively referred to as processing modules 370.

It is to be understood that the system is not intended to be limited to the components shown in FIG. 3. One or more components of the control and processing unit 300 may be provided as an external component or device. In one example non-limiting implementation, navigation engine 384 may be provided as an external navigation system that is integrated with control and processing unit 300.

Some implementations may be implemented using processor 302 without additional instructions stored in memory 304. Some implementations may be implemented using the instructions stored in memory 304 for execution by one or more general purpose microprocessors. Thus, the specification is not limited to a specific configuration of hardware and/or software.

While some implementations may be implemented in fully functioning computers and computer systems, various implementations are capable of being distributed as a computing product in a variety of forms and are capable of being applied regardless of the particular type of machine or computer readable media used to actually effect the distribution.

At least some aspects disclosed may be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache and/or a remote storage device.

A computer readable storage medium, and/or a non-transitory computer readable storage medium, may be used to store software and data which, when executed by a data processing system, causes the system to perform various methods. The executable software and data may be stored in various places including for example ROM, volatile RAM, nonvolatile memory and/or cache. Portions of this software and/or data may be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical and/or other forms of propagated signals, such as carrier waves, infrared signals, digital signals, and the like. The storage medium may comprise the internet cloud, storage media therein, and/or a computer readable storage medium and/or a non-transitory computer readable storage medium, including, but not limited to, a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB (Universal Serial Bus) keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 200, which may include control and processing unit 300, is to provide tools to a surgeon and/or a neurosurgeon that will lead to the most informed, least damaging neurosurgical operations. In addition to removal of brain tumours and intracranial hemorrhages (ICH), the navigation system 200 may also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present specification may be applied to other suitable medical procedures.

Figure 4:
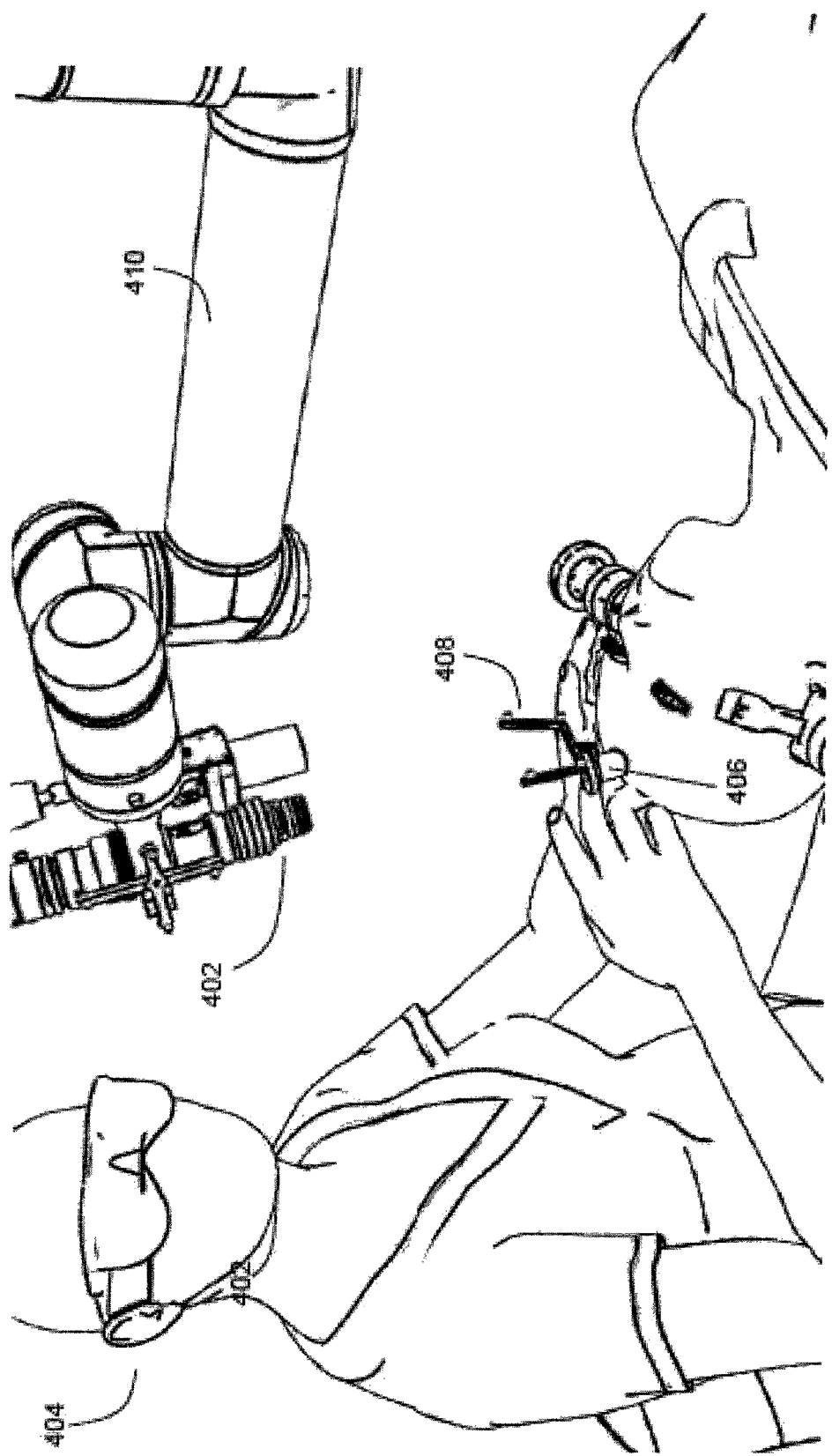
FIG. 4 depicts an example implementation port based brain surgery using a video scope, according to non-limiting implementations.

Attention is next directed to FIG. 4 which depicts a non-limiting example of a port-based brain surgery procedure using a video scope. In FIG. 4, operator 404, for example a surgeon, may align video scope 402 to peer down port 406. Video scope 402 may be attached to an adjustable mechanical arm 410. Port 406 may have a tracking tool 408 attached to it where tracking tool 408 is tracked by a tracking camera of a navigation system.

Even though the video scope 402 may comprise an endoscope and/or a microscope, these devices introduce optical and ergonomic limitations when the surgical procedure is conducted over a confined space and conducted over a prolonged period such as the case with minimally invasive brain surgery.

Figure 5:
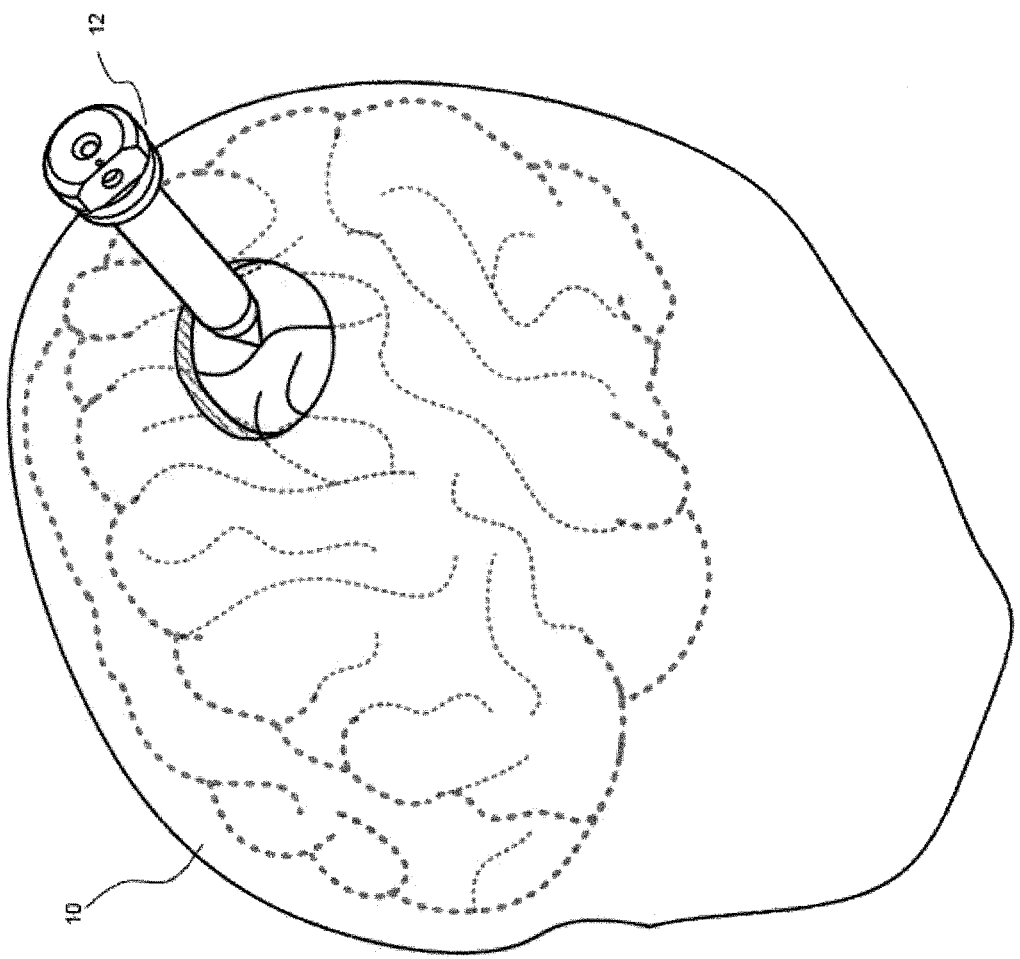
FIG. 5 depicts insertion of an access port into a human brain, for providing access to interior brain tissue during a medical procedure, according to non-limiting implementations.

FIG. 5 illustrates the insertion of an access port 12 into a human brain 10, in order to provide access to interior brain tissue during a medical procedure. In FIG. 5, access port 12 is inserted into a human brain 10, providing access to interior brain tissue. Access port 12 may include, but is not limited to, instruments such as catheters, surgical probes, and/or cylindrical ports such as the NICO BrainPath. Surgical tools and instruments may then be inserted within a lumen of the access port 12 in order to perform surgical, diagnostic or therapeutic procedures, such as resecting tumors as necessary. However, the present specification applies equally well to catheters, DBS needles, a biopsy procedure, and also to biopsies and/or catheters in other medical procedures performed on other parts of the body.

In the example of a port-based surgery, a straight and/or linear access port 12 is typically guided down a sulci path of the brain. Surgical instruments and/or surgical tools would then be inserted down the access port 12.

Figure 6:
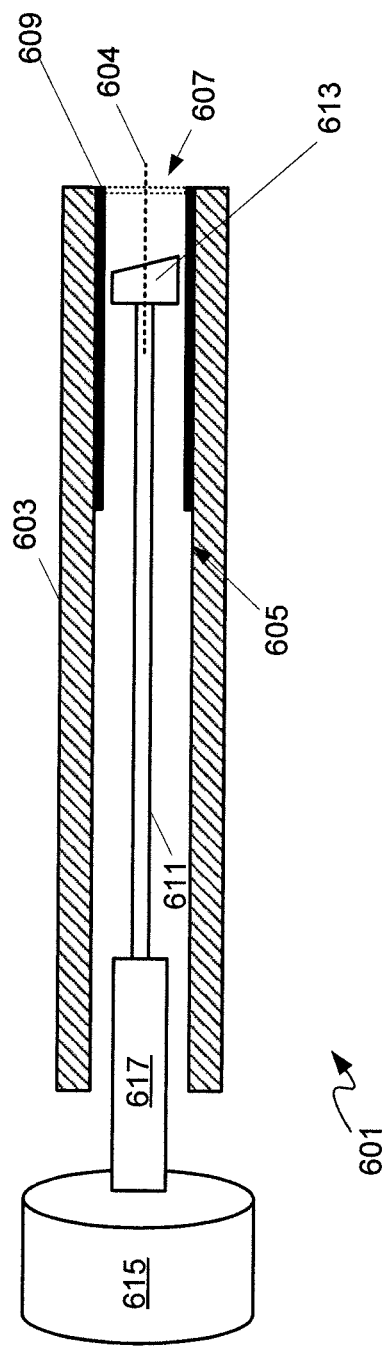
FIG. 6 depicts a forward-imaging optical coherence tomography (OCT) probe for use in a medical procedure, according to non-limiting implementations.

Attention is next directed to FIG. 6, which depicts an example of a surgical tool that could be used with and/or in place of access port 12.

Specifically, FIG. 6 a forward-imaging optical coherence tomography (OCT) probe 601 for use in a medical procedure, comprising: a substantially cylindrical housing 603 (depicted in cross-section in FIG. 6) comprising: a longitudinal axis 604; an interior side 605; a distal end 607 that is optically transparent; and a mirror 609 (also depicted in cross-section in FIG. 6) located at interior side 605, adjacent distal end 607; an optical fiber 611 located inside cylindrical housing 603 along longitudinal axis 604; a wedge lens 613 located inside cylindrical housing 603, wedge lens 613 configured to receive light from optical fiber 611, and direct the light towards mirror 609; and, at least one motor 615 configured to both: rotate optical fiber 611 and wedge lens 613 about longitudinal axis 604 and inside cylindrical housing 603; and, linearly displace optical fiber 611 and wedge lens 613 along longitudinal axis 604 and inside cylindrical housing 603; mirror 609 configured to: receive light from wedge lens 613 and reflect the light out of distal end 607 as wedge lens 613 moves linearly and rotationally. For clarity, forward-imaging optical coherence tomography (OCT) probe 601 will be interchangeably referred to hereafter as probe 601; similarly, optical fiber 611 will be interchangeably referred to hereafter as fiber 611; further, at least one motor 615 will be interchangeably referred to hereafter as motor 615.

As depicted, probe 601 further comprises an optional second optical fiber 617 (interchangeably referred to hereafter as fiber 617) mechanically coupling fiber 611 to motor 615, and optically coupling fiber 611 to an OCT interferometer, for example. However, in other implementations motor 615 can move fiber 611 without the use of intervening fiber 617, and fiber 611 can be coupled to an OCT interferometer.

While not depicted, probe 601 can further comprise a power supply configured to power at least at least one motor 615. Furthermore, while not depicted, probe 601 can further comprise one or more computing devices configured to one or more of: control at least one motor 615; and process OCT images received back from the optical fiber 611 as the optical fiber 611 is moving. Alternatively, such a power supply can be provided independently of probe 601.

While not depicted, probe 601 can further comprise a at least one OCT interferometer in communication with optical fiber 611, for example to provide light to fiber 611, and to receive images from a sample and/or target illuminated by probe 601.

Furthermore, end 607 can generally comprise a window (depicted in stippled lines), a film a coating and the like, including that is generally transparent to OCT light; such a window can include, but is not limited to, anti-reflective coatings. However, end 607 generally includes a partial-reflection coating and/or film to provide a common path reference beam. In particular, OCT systems generally function by recording optical interference of light from a sample arm and a reference arm which is detected by a photodetector, and the optical path difference between the two arms presents the depth information which is encoded in an optical interference pattern. Hence, while not depicted, end 607 generally comprises a partial-reflection coating and/or film, so that a first portion of light emitted from wedge lens 613 will reflect back as a reference signal while a second portion of light emitted from wedge lens 613 will propagate to the tissue to serve as sample signal. Hence, the optical path difference of each imaging point is the path difference between the end 607 and an imaging plane, which generally loosens requirements for a focal depth of wedge lens 613 and associated recovery algorithms.

Mirror 609 can comprise a ring mirror, a cylindrical mirror, a reflection film and the like.

Figure 7:
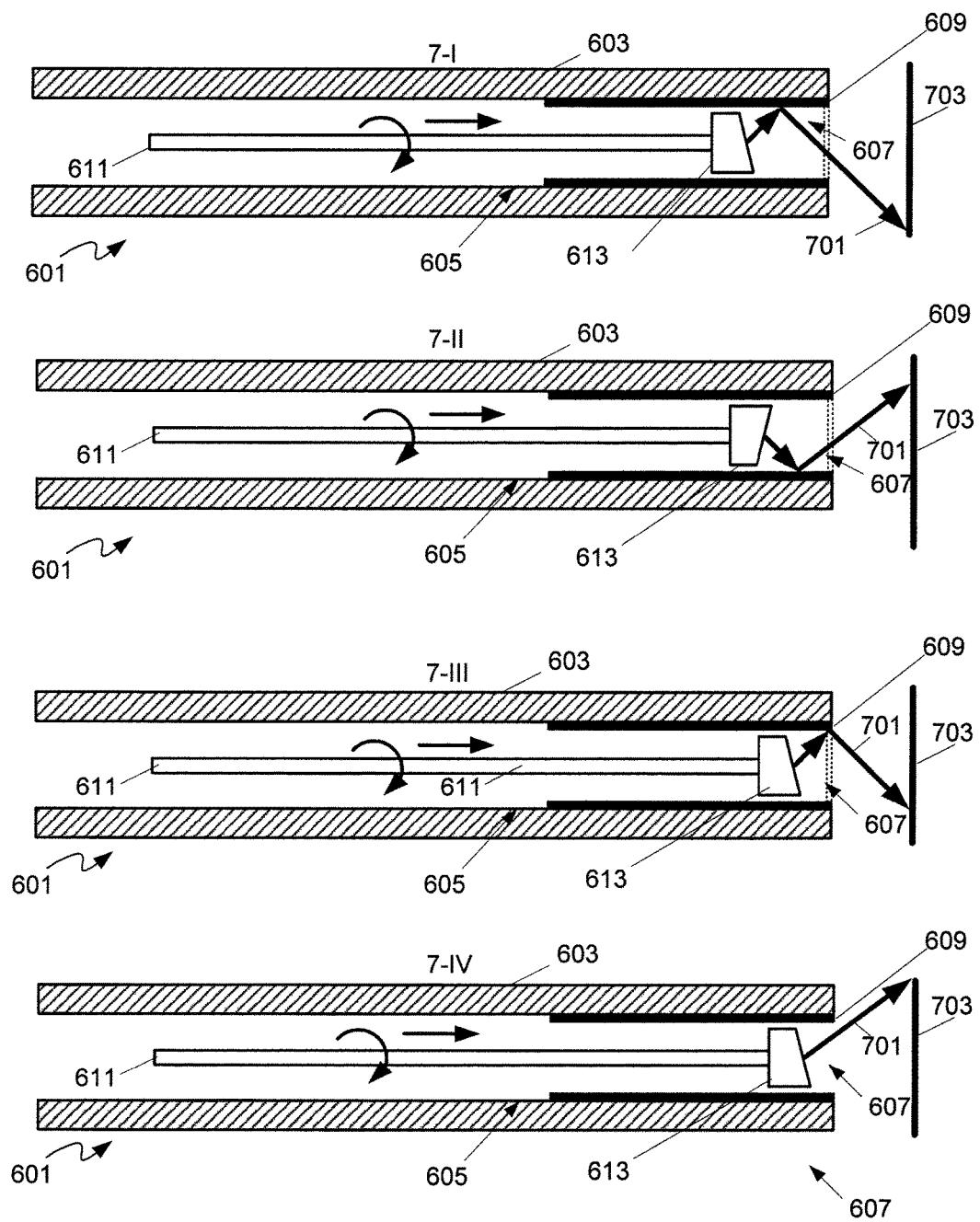
FIG. 7 depicts probe of FIG. 6 as a position of a wedge lens changes, according to non-limiting implementations.

Attention is next directed to FIG. 7, which depicts views 7-I, 7-II, 7-III, 7-IV of details of probe 601 as motor 615 (not depicted) rotates and linearly moves wedge lens 613 towards end 607, through housing 603 and past mirror 609, while emitting light 701 at an angle to longitudinal axis 604 (not depicted), and towards mirror 609. While not all features of probe 601 are depicted, it is assumed that each feature depicted in FIG. 6 is nonetheless present. Also depicted in FIG. 7 is a target 703 located adjacent end 607, light 701 being emitted out of end 607 towards target 703. Target 703 generally comprises one or more of a sample, tissue and the like being imaged by probe 601. Hence, while target 703 is depicted in a side profile, and as flat for clarity, target 703 is generally textured and/or three-dimensional.

In each of views 7-I, 7-II, 7-III, 7-IV it is assumed that light 701 is conveyed to wedge lens 613 by fiber 611 and that wedge lens 613 emits light 701 at an angle to longitudinal axis 604. In each of views 7-I, 7-II, 7-III, light 701 reflects from mirror 609 towards target 703 while rotating and being moved towards end 607, and in view 7-IV, wedge lens 613 is at a position relative to end 607 where light 701 is emitted from end 607 without reflecting from mirror 609. Furthermore, from view 7-I to view 7-II wedge lens 613 is rotated by 180°, from view 7-II to view 7-III wedge lens 613 is again rotated by 180°, and from view 7-III to view 7-IV wedge lens 613 is again rotated by 180°. In addition, from view 7-I to view 7-II to view 7-III, an illumination position of light 701 onto target 703 gets closer and closer to a center of target 703. As in view 7-IV, light 701 does not reflect from mirror 609, light 607 an illumination position of light 701 onto target 703 is further away from a center of target 703, relative to view 7-III.

Hence, in general, as wedge lens 613 is rotated and is moved towards end 607, light 701 illuminates target 703 in a spiral until view 7-IV occurs. Alternatively, wedge lens 613 can be positioned at a plurality of linear positions, and rotated at each linear position to inscribe a ring of illumination and/or a circle of illumination on target 703 at each linear position.

It is further assumed that there is a position of wedge lens 613, relative to end 607, where light 701 reflected from mirror 609 starts to reflect from mirror 609 out of end 607 upon one reflection and when wedge lens 613 is further away from end 607, light 701 will reflect from mirror 609 out of end 607 using multiple reflections.

It is further assumed in FIG. 7 that once target 703 is illuminated, light reflected from target 703 is collected by wedge lens 613 and conveyed out of probe 601 by fiber 611 for analysis by an OCT interferometer and the like. Hence, at each position of wedge lens 613, an OCT image point is acquired, which can be assembled into an OCT image.

Figure 8:
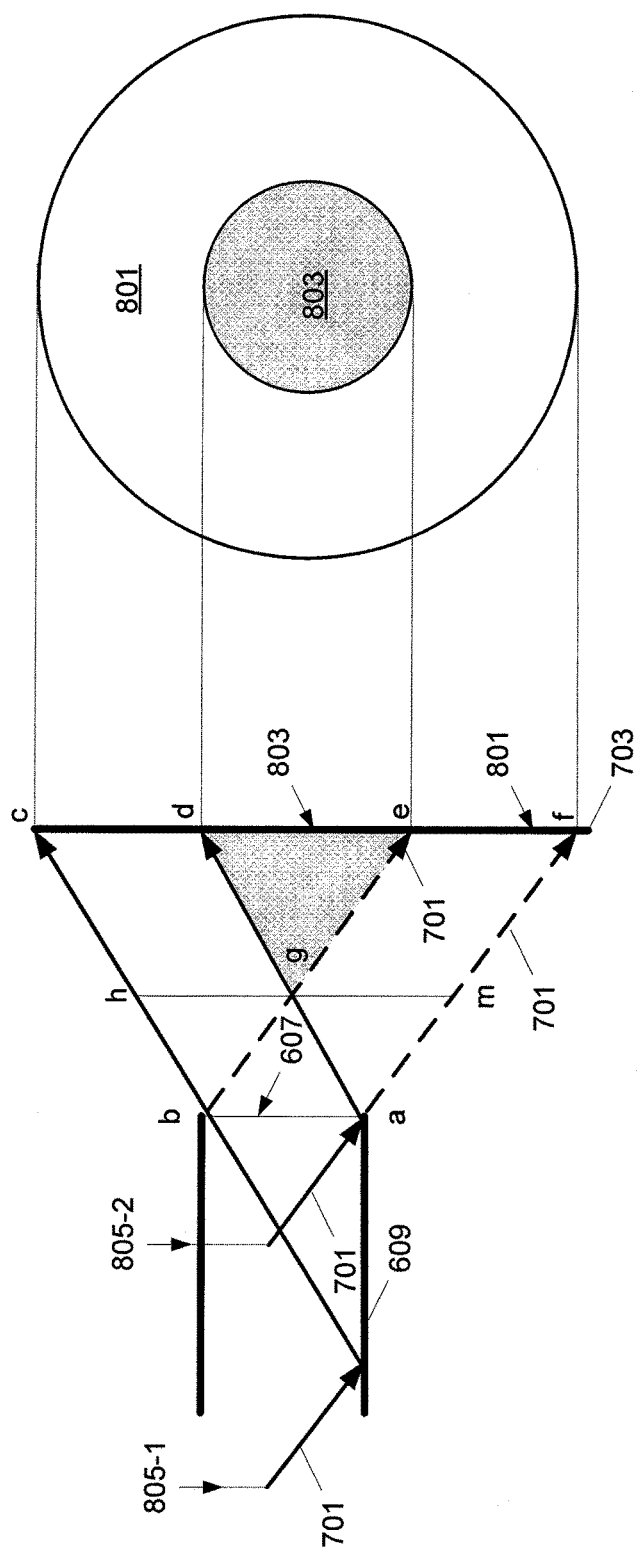
FIG. 8 depicts an imaging area of the probe of FIG. 6, according to non-limiting implementations.

Attention is next directed to FIG. 8 which depicts an imaging area 801 of probe 601 onto target 703 as wedge lens 613 moves through mirror 609. While wedge lens 613 is not depicted, light 701 emitted from wedge lens 613 is depicted as interacting with mirror 609 at a first position 805-1, where light 701 starts to reflect out of end 607 after one reflection from mirror 609, and a second position 805-2, just before light 701 starts to exit end 607 without reflecting from mirror 609. For clarity locations, a, b, c, d, e, f, g, h and m are indicated in FIG. 8 to further a discussion of imaging area 801 as follows.

Light 701 depicted in solid lines in FIG. 8 shows a path of light 701 at each position 805-1, 805-2 when wedge lens 613 emits light "downwards", though it is appreciated that the term "downwards" is used only in reference to FIG. 8 and is not intended to imply that light 701 is moving downwards relative to the ground and/or the Earth. In particular, light emitted along path "bc" shows a path of light 701 exiting end 607 when wedge lens 613 is a position 805-1, and light 701 is emitted downwards, and light emitted along path "ad" shows a path of light 701 exiting end 607 when wedge lens 613 is a position 805-2, and light 701 is emitted downwards.

Light 701 depicted in stippled lines in FIG. 8 shows a path of light 701 at each position 805-1, 805-2 when wedge lens 613 is rotated by 180° around longitudinal axis 604, though only the path of light 701 exiting end 607 in this position is shown for clarity; however it is assumed that such light 601 follows same path as light 701 depicted in solid lines, but rotated by 180° around longitudinal axis 604. In particular, light emitted along path "af" shows a path of light 701 exiting end 607 when wedge lens 613 is a position 805-1, rotated by 180° around longitudinal axis 604, and light emitted along path "be" shows a path of light 701 exiting end 607 when wedge lens 613 is a position 805-2, but rotated by 180° around longitudinal axis 604.

Hence, by rotating wedge lens 613 by 360°, an image volume "abcf" is illuminated, with a "missing" image holed "gde". However, the image volume "abhm" is fully covered with triangle "abg" which is imaged twice. Such double imaging can be resolved using a computing device processing images collected by an OCT interferometer.

Hence, when target 703 is located at a position within triangle "abg", there are no holes in the coverage. However, when target is located in the triangle "gde", as depicted, an imaging area 801 is inscribed, with a hole 803 in the center. In other words, imaging area 801 can comprise an annulus.

Figure 9:
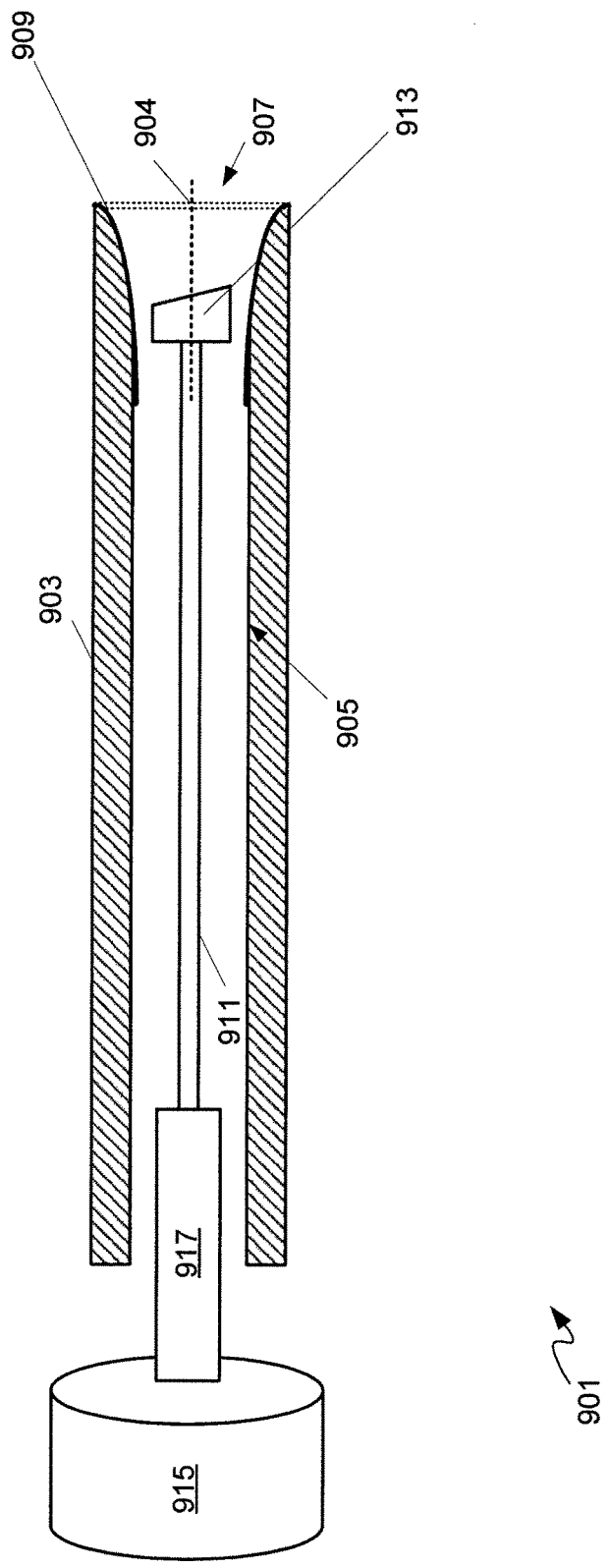
FIG. 9 depicts a forward-imaging optical coherence tomography (OCT) probe for use in a medical procedure, according to alternative non-limiting implementations.

In particular, in implementations described heretofore, mirror 609 comprises a ring mirror, for example, with a radius and/or diameter similar to a respective radius and/or diameter of cylindrical housing 603. However, such a ring mirror can result in a hole 803 in imaging area 801 as shown in FIG. 8. To address this, an alternative probe 901 is depicted in FIG. 9, which is substantially similar to probe 601, with like elements having like numbers, however in a "900" series rather than a "600" series. In particular probe 901 comprises: a substantially cylindrical housing 903 (depicted in cross-section in FIG. 9) comprising: a longitudinal axis 904; an interior side 905; a distal end 907 that is optically transparent; and a mirror 909 (also depicted in cross-section in FIG. 9) located at interior side 905, adjacent distal end 907; a optical fiber 911 located inside cylindrical housing 903 along longitudinal axis 904; a wedge lens 913 located inside cylindrical housing 903, wedge lens 913 configured to receive light from optical fiber 911, and direct the light towards mirror 909; and, at least one motor 915 configured to both: rotate optical fiber 911 and wedge lens 913 about longitudinal axis 904 and inside cylindrical housing 903; and, linearly displace optical fiber 911 and wedge lens 913 along longitudinal axis 904 and inside cylindrical housing 903; mirror 909 configured to: receive light from wedge lens 913 and reflect the light out of distal end 907 as wedge lens 913 moves linearly and rotationally. Furthermore, probe 901 comprises optical fiber 917 similar to optical fiber 617.

However, in contrast to mirror 609, where the reflection angle is constant regardless of a position of wedge lens 613 relative to end 607, mirror 909 comprises a graded-radius cylindrical reflection mirror 909, with a widest radius adjacent distal end 607, with housing 903 adapted to a shape of mirror 909 when mirror 909 cannot otherwise be fitted at housing 903. As the radius of mirror 909 varies, the reflection angle of light from wedge lens 913 varies, depending on a position of wedge lens 913 relative to end 907.

Figure 10:
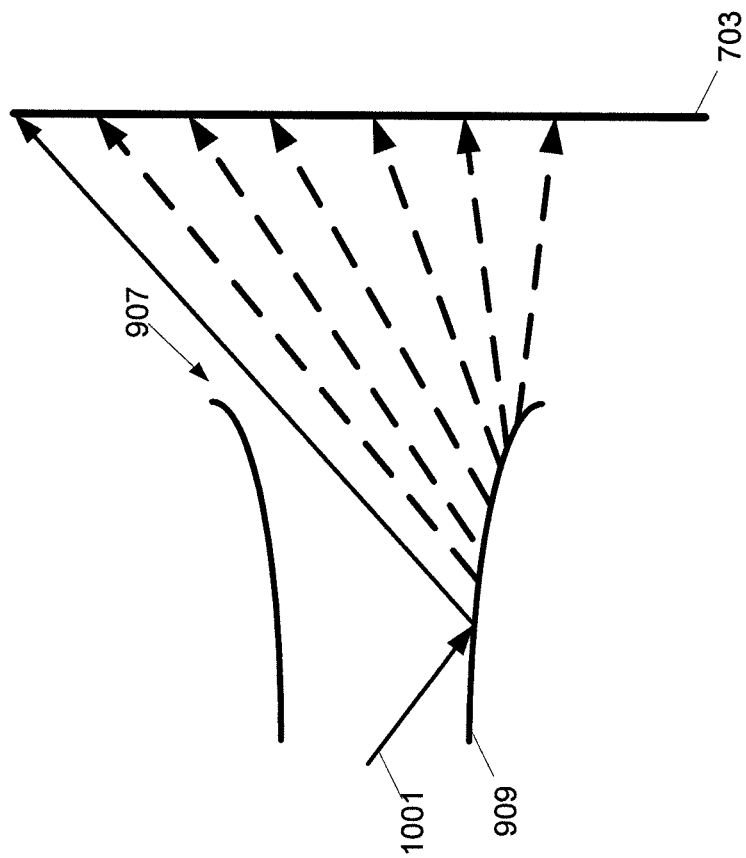
FIG. 10 depicts an imaging area of the probe of FIG. 9, according to non-limiting implementations.

In any event, with reference to FIG. 10, which depicts light 1001 emitted from wedge lens 913 reflecting from mirror 909 at various positions, and reflecting onto target 703, there are no holes in the coverage. For example light 1001 depicted in solid lines shows a light path of light 1001 onto target 703 when wedge lens 913 is at a position where light 1001 starts to exit end 907 after one reflection (analogous to position 805-1 of FIG. 8), and light 1001 depicted in stippled lines shows light paths of light 1001 as wedge lens 913 is moved towards end 907, and the reflection angle changes with location. It is assumed in FIG. 10 that wedge lens 913 is in the same rotational position for each light path, and when wedge lens 913 is rotated by 180° a circular imaging area is inscribed on target 703.

Figure 11:
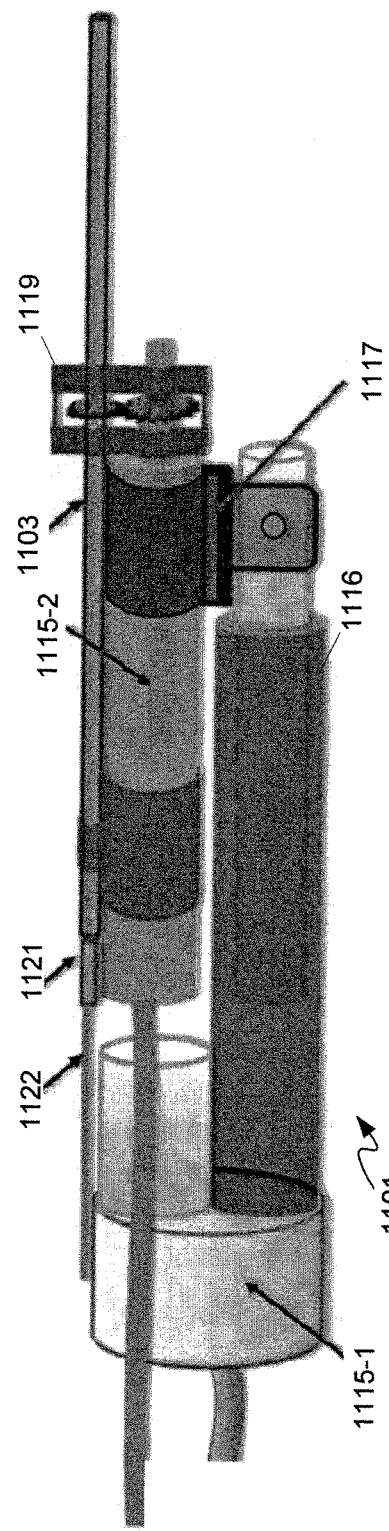
FIGS. 11A and 11B depicts a forward-imaging optical coherence tomography (OCT) probe for use in a medical procedure, according to yet further alternative non-limiting implementations.
Figure 11:
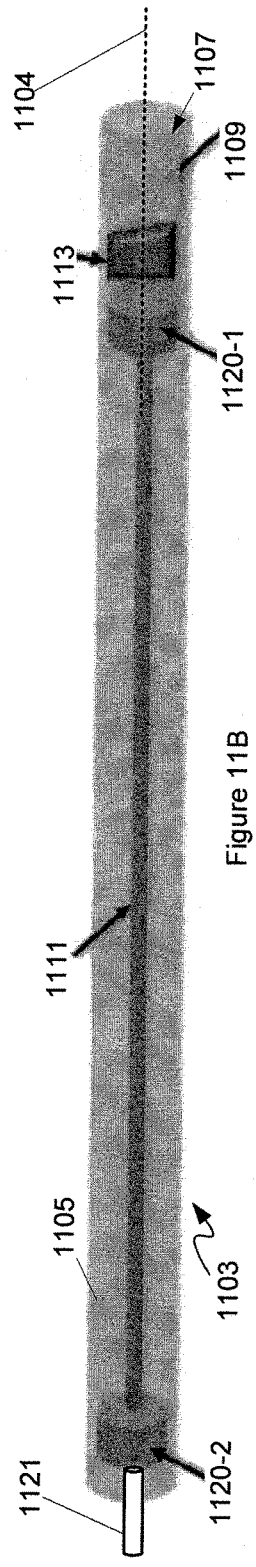
Figure 12:
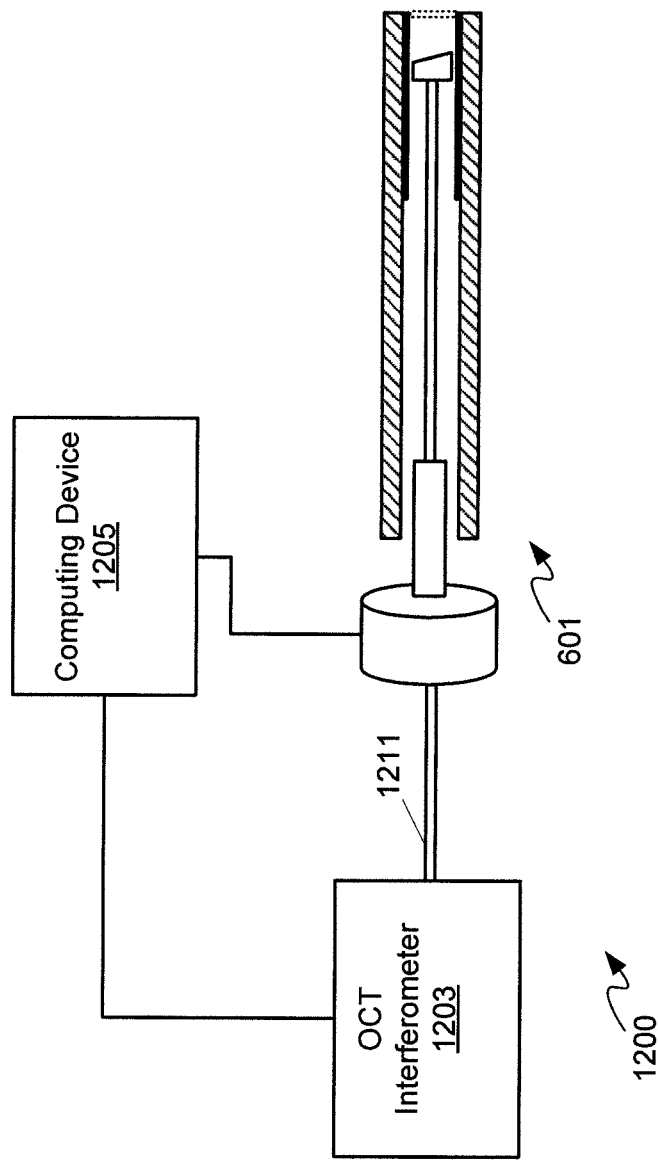
FIG. 12 depicts an OCT system that includes the probe of FIG. 6, according to alternative non-limiting implementations.

Attention is next directed to FIG. 11A and FIG. 11B which depicts a specific non-limiting implementation of a probe 1101 similar to probe 601, with like elements having like numbers, however in a "1100" series rather than a "600" series. In particular FIG. 11A depicts an external view of probe 1101, and FIG. 11B depicts detail inside a housing 1103 of probe 1101. In general, probe 1101 comprises: a substantially cylindrical housing 1103 (an interior of which is depicted in FIG. 11A) comprising: a longitudinal axis 1104; an interior side 1105; a distal end 1107 that is optically transparent; and a mirror located at interior side 1105, adjacent distal end 1107; a optical fiber 1111 located inside cylindrical housing 1103 along longitudinal axis 1104; a wedge lens 1113 located inside cylindrical housing 1103, wedge lens 1113 configured to receive light from optical fiber 1111, and direct the light towards mirror 1109; and, at least one motor 1115-1, 115-2 configured to both: rotate optical fiber 1111 and wedge lens 1113 about longitudinal axis 1104 and inside cylindrical housing 1103; and, linearly displace optical fiber 1111 and wedge lens 1113 along longitudinal axis 1104 and inside cylindrical housing 1103; mirror 1109 configured to: receive light from wedge lens 1113 and reflect the light out of distal end 1107 as wedge lens 1113 moves linearly and rotationally.

In particular, at least one motor 1115-1, 1115-2 comprises a linear motor 1115-1, and a rotational motor 1115-2 coupled to an arm 1116 being moved by linear motor 1115-1 via a joint connector 1117. Rotational motor 1115-2 is coupled to housing 1103 via a gear and fix joint mechanism 1119. Hence, linear motor 1115-1 moves arm 1116, rotational motor 1115-2, mechanism 1119 and housing 1103 linearly (and hence fiber 1111 and wedge lens 1113), and rotational motor 1115-2 simultaneously rotates housing 1103 linearly (and hence fiber 1111 and wedge lens 1113). Each of motors 1115-1, 1115-2 are configured to be controlled independently such that a linear position and a rotational position of wedge lens 1113 can each be controlled independently.

Furthermore, as depicted in FIG. 11B, probe 1101 further comprises at least one GRIN (graded index) lens 1120-1 between an exit face of fiber 1111 and wedge lens 1113, the at least one GRIN lens 1120-1 configured to focus the light from the exit face into wedge lens 1113.

As depicted in FIG. 11A, probe 1101 further comprises an optical coupler 1121 configured to couple a second optical fiber 1122 to an entrance face of fiber 1111, second optical fiber 1122 configured to convey the light from an OCT interferometer to fiber 1111. In some implementations, as depicted in FIG. 11B, probe 1101 further comprises at least one GRIN lens 1120-2 between optical coupler 1121 and the entrance face of fiber 111, at least one GRIN lens 1120-2 configured to focus the light from optical coupler 1121 into fiber 1111.

In general, each GRIN lens 1120-1, 1120-1 receives collimated light and focuses the collimated light towards a focal point, which generally serves to address alignment issues within probe 1101. Furthermore, each GRIN lens 1120-1, 1120-1 can be provided independent of the other GRIN lens 1120-1, 1120-1; for example, probe 1101 can comprise GRIN lens 1120-1 or GRIN lens 1120-2, or both GRIN lenses 1120-1, 1120-2.

Attention is next directed to system 1200 which comprises probe 601, an OCT interferometer 1203 and a computing device 1205. Computing device 1205 can comprise control and processing unit 300. In general, OCT interferometer 1203 is in communication with probe 601 via an optical fiber 1211. Furthermore, computing device 1205 is configured to: receive and process OCT images from OCT interferometer 1203, as well as control probe 601, for example by controlling motor 615 to position wedge lens 613 relative to end 607 to illuminate a sample and/or target with OCT light and collect OCT images therefrom. Hence, computing device 1205 can be provisioned with a look up table that correlates settings for motor 615 with positions of wedge lens 613 so that a plurality OCT image points can be received and processed from OCT interferometer 1203 to generate an image of the sample and/or target from the plurality OCT image points based on the respective positions of wedge lens 613 at which each of the plurality OCT image points was acquired. Furthermore, prove 601 can be replaced with other similar probes, for example probe 1101.

Figure 13:
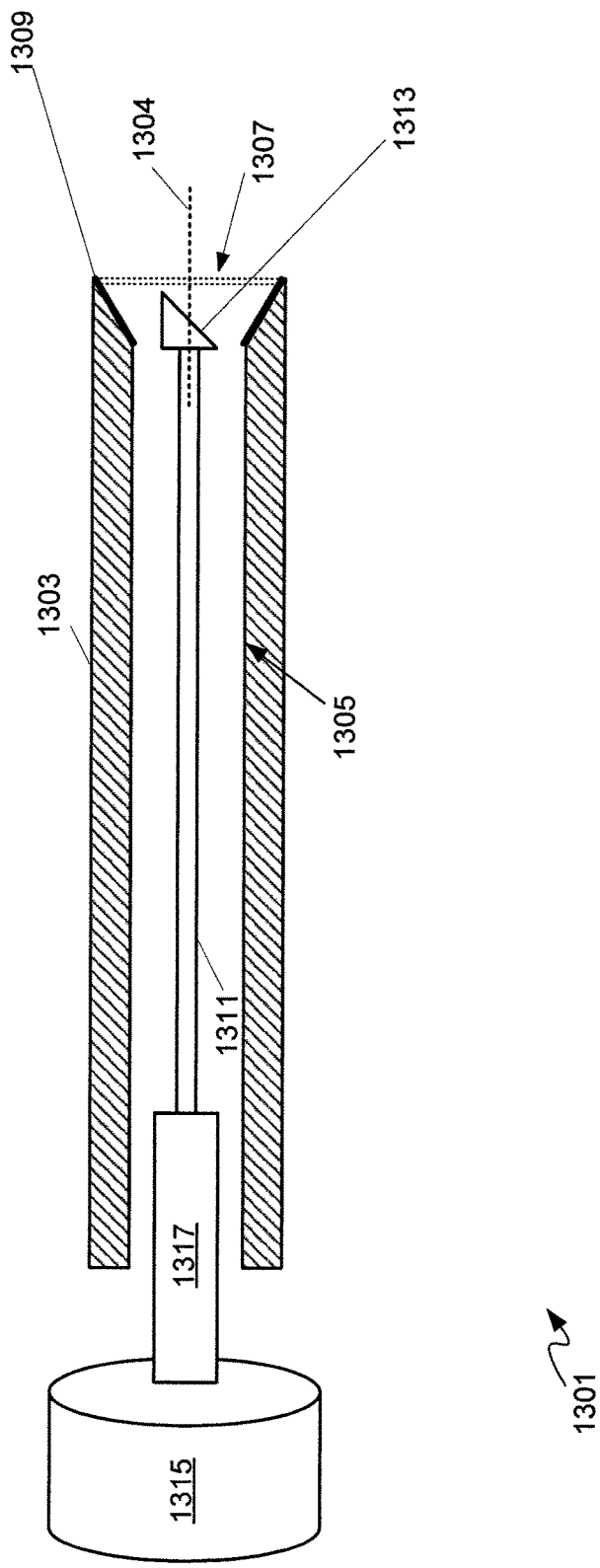
FIG. 13 depicts a forward-imaging optical coherence tomography (OCT) probe for use in a medical procedure, according to alternative non-limiting implementations.

Attention is next directed to FIG. 13, which depicts an alternative probe 1301, which is substantially similar to probe 601, with like elements having like numbers, however in a "1300" series rather than a "600" series. In particular probe 1301 comprises: a substantially cylindrical housing 1303 (depicted in cross-section in FIG. 13) comprising: a longitudinal axis 1304; an interior side 1305; a distal end 1307 that is optically transparent; and a mirror 1309 (also depicted in cross-section in FIG. 13) located at interior side 1305, adjacent distal end 1307; an optical fiber 1311 located inside cylindrical housing 1303 along longitudinal axis 1304; a wedge lens 1313 located inside cylindrical housing 1303, wedge lens 1313 configured to receive light from optical fiber 1311, and direct the light towards mirror 1309; and, at least one motor 1315 configured to both: rotate optical fiber 1311 and wedge lens 1313 about longitudinal axis 1304 and inside cylindrical housing 1303; and, linearly displace optical fiber 1311 and wedge lens 1313 along longitudinal axis 1304 and inside cylindrical housing 1303; mirror 1309 configured to: receive light from wedge lens 1313 and reflect the light out of distal end 1307 as wedge lens 1313 moves linearly and rotationally. Furthermore, probe 1301 comprises optical fiber 1317 similar to optical fiber 617.

However, in contrast to mirror 609, which is substantially parallel to longitudinal axis 604, mirror 1309 is at about a 45° to longitudinal axis 1304. Furthermore, wedge lens 1313 is configured to receive light from optical fiber 1311, and direct the light towards mirror 1309 at about 90° to longitudinal axis 1304.

Figure 14:
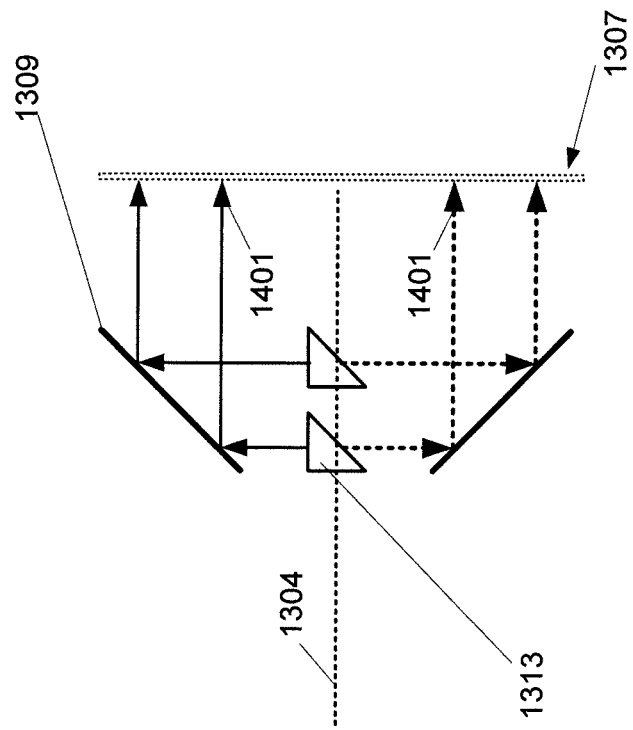
FIG. 14 depicts paths of light through the probe of FIG. 9, according to non-limiting implementations.

For example, attention is FIG. 14 which depicts light 1401 emitted from wedge lens 1313 reflecting from mirror 1309 at two positions along longitudinal axis 1304, and reflecting to end 1307; while not depicted, it is assumed that at least a portion light 1401 continues through end 1307 to a target. Furthermore, light 1401 depicted in sold lines indicates light emitted from wedge lens 1313 in a first direction (e.g. up with regards to FIG. 14), and light 1401 depicted in stippled lines indicates light emitted from wedge lens 1313 in a second direction perpendicular to the first direction (e.g. down with regards to FIG. 14). In other words, paths of light 1401 are shown in two directions at each of the first position and the second position (e.g. as wedge lens 1313 is moved linearly along longitudinal axis), as wedge lens 1313 is rotated.

In any event, as is clear from FIG. 14, as light 1401 is emitted at 90° to longitudinal axis 1304, and as mirror 1309 is at 45° to longitudinal axis 1304, and as wedge lens 1313 is centered on longitudinal axis 1304, a length of a path of light 1401 between wedge lens 1313 and end 1307 is constant regardless of a position and/or a rotational position of wedge lens 1313. For example, in implementations described above, a correction for light path length can be applied as a length of a path of light can vary with position of a wedge lens; such a correction is obviated with probe 1301, however, as is also clear from FIG. 14, side-imaging doesn't occur.

Figure 15:
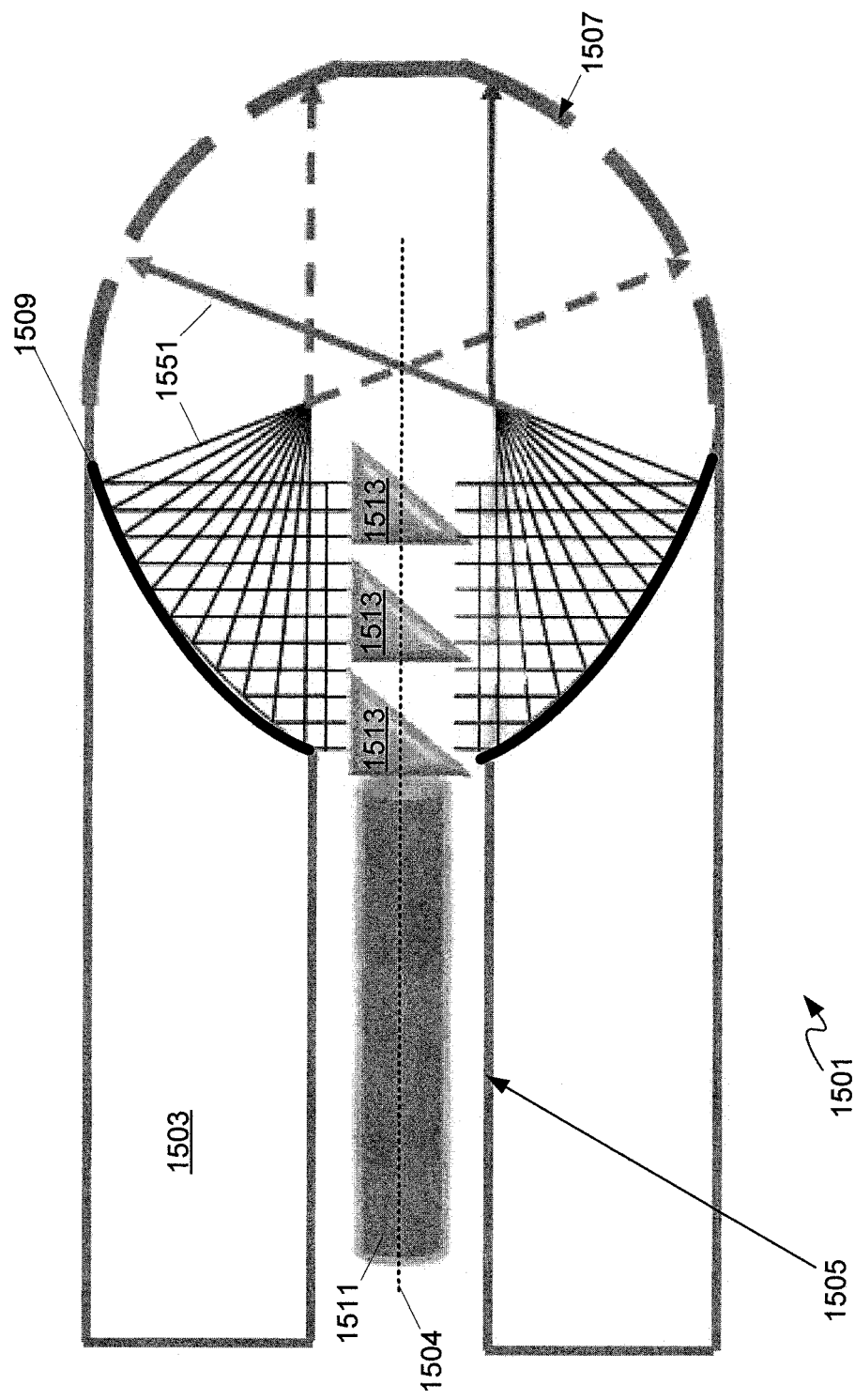
FIG. 15 depicts a portion of a forward-imaging optical coherence tomography (OCT) probe for use in a medical procedure, according to alternative non-limiting implementations.

Hence, attention is next directed to FIG. 15, which depicts portions of an alternative probe 1501, which is substantially similar to probe 1301, with like elements having like numbers, however in a "1500" series rather than a "1300" series. In particular probe 1501 comprises: a substantially cylindrical housing 1503 (depicted in cross-section in FIG. 15) comprising: a longitudinal axis 1504; an interior side 1505; a distal end 1507 that is optically transparent; and a mirror 1509 (also depicted in cross-section in FIG. 15) located at interior side 1505, adjacent distal end 1507; an optical fiber 1511 located inside cylindrical housing 1503 along longitudinal axis 1504; a wedge lens 1513 located inside cylindrical housing 1503 (and depicted at three different positions along longitudinal axis 1504), wedge lens 1513 configured to receive light from optical fiber 1511, and direct the light towards mirror 1509; and, at least one motor (not depicted, but similar to motor 1315) configured to both: rotate optical fiber 1511 and wedge lens 1513 about longitudinal axis 1504 and inside cylindrical housing 1503; and, linearly displace optical fiber 1511 and wedge lens 1513 along longitudinal axis 1504 and inside cylindrical housing 1503; mirror 1509 configured to: receive light from wedge lens 1513 and reflect the light out of distal end 1507 as wedge lens 1513 moves linearly and rotationally. Furthermore, probe 1501 comprises an optical fiber (not depicted) similar to optical fiber 1317. Also depicted in FIG. 15 are paths of light 1551 as light 1551 is conveyed by wedge lens 1513 to mirror 1509 to end 1507 at various positions and orientations of wedge lens 1513.

However, in contrast to probe 1301, mirror 1509 is parabolic, with a widest radius adjacent distal end 1507 (and hence concave relative to longitudinal axis 1504), as well as being centered along longitudinal axis 1504. Furthermore, end 1507 is also parabolic. Such a geometry ensures that a path length of light 1551 between wedge lens 1513 and end 1507 is constant regardless of position and/or orientation of wedge lens 1513. Furthermore, as mirror 1509 is parabolic, both side imaging and forward imaging occurs.

Figure 16:
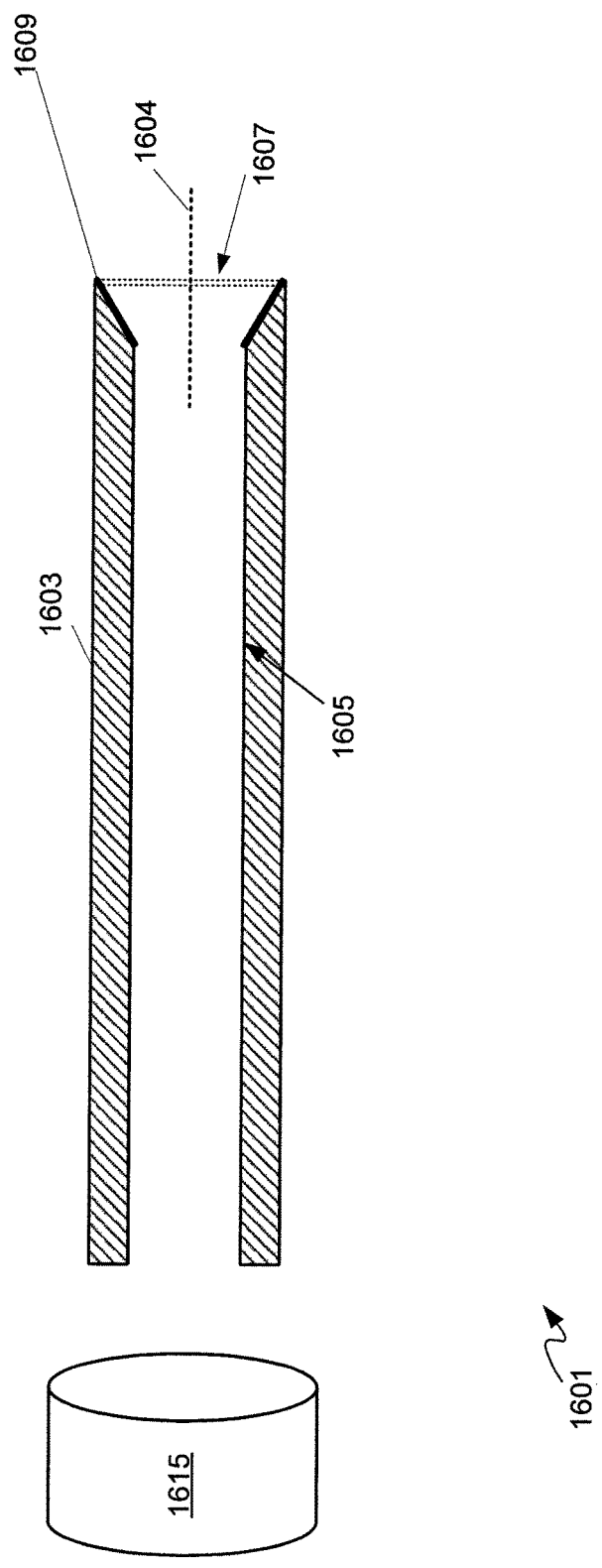
FIG. 16 depicts a kit for adapting an OCT probe for depth and surface profiling, the OCT probe comprising an optical fiber in optical communication with a wedge lens, according to alternative non-limiting implementations.

Attention is next directed to FIG. 16 which depicts a kit 1601 kit for adapting an OCT probe for depth and surface profiling, the OCT probe comprising a optical fiber in optical communication with a wedge lens, kit 1601 comprising: a cylindrical housing 1603 comprising: a longitudinal axis 1604; an interior side 1605; a distal end 1607 that is optically transparent; and a mirror 1609 located at interior side 1605, adjacent distal end 1607; cylindrical housing 1603 configured to accept therein: the optical fiber located along longitudinal axis 1604; and, the wedge lens located inside adjacent distal end 1607, mirror 1609 configured to: receive light from the wedge lens and reflect the light out of distal end 1607; and, at least one motor 1615 connectable to the optical fiber, at least one motor 1615 configured to both: rotate the optical fiber and the wedge lens about longitudinal axis 1604 and inside cylindrical housing 1603; and, linearly displace the optical fiber and the wedge lens along the longitudinal axis 1604 and inside cylindrical housing 1603; mirror 1609 configured to: receive light from the wedge lens and reflect the light out of distal end 1607 as the wedge lens moves linearly and rotationally. In other words, components of kit 1601 can be used to build probe 601. Alternatively, kit 1601 can comprise components that can be used to build probe 1101. In particular, as existing OCT probes tend to be side probes, mirror 1609 is similar to mirror 1309, and hence is at a 45° angle to longitudinal axis 1604; hence kit 1601 can comprise a kit for adapting a side imaging OCT probe to a forward imaging OCT probe.

Hence, while not depicted, kit 1601 can further comprise one or more of: a second optical fiber, similar to optical fiber 617; and/or optical fiber 1122, an optical coupler, similar to optical coupler 1121; and/or other components that can attach housing 1603 to motor 1615, similar to arm 1116, joint connector 1117 and/or fix joint mechanism 1119.

Furthermore, kit 1601 can be adapted to include a mirror similar to mirror 1509 such that kit 1601 is configured to adapt a side imaging OCT probe a side imaging and forward imaging OCT probe.

In any event, provided herein is an OCT probe that includes a single mode fiber "SMF") with a wedge lens located at a distal end. The SMF is mounted on a linear rotary motor which provides linear and rotary moving simultaneously. A substantially cylindrical housing includes an optically transparent end, with a mirror located on an interior side at the distal end, the SMF and the wedge lens located inside the housing. At the same time, the optically transparent end comprises an optical window with reflection film to provide a common path reference beam. Hence, despite the difference of the optical path length of each imaging point, the reference plane and the imaging plane has constant distance.

In general, light is guided inside the SMF to the wedge lens. The wedge lens tilts the beam angle away from longitudinal axis, and the mirror then reflects the light out the end to illuminate a target and/or a sample. At a given linear position, the linear rotary motor rotates the SMF and the wedge lens, to inscribe a circular data collection path on the target and/or sample. The linear rotary motor moves the wedge lens forward (or backward), and the light move to a different place on the target and/or sample to image a smaller or larger circle by again rotating the wedge lens. Thus, by using a linear rotary motor, probes described herein can forward image objects.

Furthermore, models of a prototype of probes described herein show that a diameter of the SMF with wedge lens can be made as small as about 125 μm. Thus, with the housing, the overall diameter is similar to that of a side-imaging probe (about 400 μm). Hence, a forward imaging probe described herein as both the advantages of a conventional side-imaging probes and conventional forward imaging probes.

While features of OCT probes described with reference to specific implementations, features described with reference to one implementation of an OCT probe may be used with other implementations of OCT probes. For example, any of the OCT probes described herein may be adapted to include anti-reflective coatings, immersion materials, index matching materials, tracking devices, and the like.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A kit for adapting a side imaging Optical Coherence Tomography (OCT) probe for both forward imaging and side imaging, the OCT probe comprising an optical fiber in optical communication with a wedge lens, the kit comprising:
    a cylindrical housing comprising: a longitudinal axis; an interior side; a distal end that is optically transparent; and a parabolic ring mirror located at the interior side, adjacent the distal end, and a widest radius of the parabolic ring mirror being disposed adjacent the distal end, wherein an interior surface of the parabolic ring mirror defines a volume of space within the cylindrical housing; the cylindrical housing configured to accept the OCT probe therein such that:
        the optical fiber is located along the longitudinal axis of the cylindrical housing and disposed within the volume of space; and,
        the wedge lens is located inside the cylindrical housing and disposed within the volume of space, adjacent the distal end; and,
    at least one motor connectable to the optical fiber, the at least one motor configured to both:
        rotate the optical fiber and the wedge lens about the longitudinal axis of the cylindrical housing and inside the volume of space; and,
        linearly displace the optical fiber and the wedge lens along the longitudinal axis and inside the volume of space;
    the parabolic ring mirror configured to, when the OCT probe is accepted in the volume of space: receive light from the wedge lens and reflect the light out of the distal end as the wedge lens moves linearly and rotationally.

2. The kit of claim 1, further comprising at least one graded index (GRIN) lens configured for location between an exit face of the optical fiber and the wedge lens, the at least one GRIN lens configured to focus light from the exit face into the wedge lens.

3. The kit of claim 1, wherein the optical fiber comprises a first optical fiber, the kit further comprising an optical coupler configured to couple a second optical fiber to an entrance face of the first optical fiber, the second optical fiber configured to convey light from an OCT interferometer to the first optical fiber.

4. The kit of claim 3, further comprising at least one graded index (GRIN) lens configured for location between the optical coupler and the entrance face of the first optical fiber, the at least one GRIN lens configured to focus light from the optical coupler into the first optical fiber.

5. The kit of claim 1, wherein the at least one motor comprises a linear motor and a rotational motor.

* * * * *